United States Patent [19]

Eckert

[11] Patent Number: 4,563,895

[45] Date of Patent: Jan. 14, 1986

[54] APPARATUS AND METHOD FOR ULTRASONIC DETECTION OF INCLUSIONS IN MOLTEN METALS

[75] Inventor: Charles E. Eckert, Plum Boro, Pa.

[73] Assignee: Aluminum Company of America, Pittsburgh, Pa.

[21] Appl. No.: 642,488

[22] Filed: Aug. 20, 1984

[51] Int. Cl.[4] ............................................. G01N 29/02
[52] U.S. Cl. ...................................... 73/61 R; 73/644
[58] Field of Search ................................. 73/61 R, 644

[56] References Cited

U.S. PATENT DOCUMENTS

| | | | |
|---|---|---|---|
| 3,320,797 | 5/1967 | Tajiri et al. | 73/67.7 |
| 3,444,726 | 5/1969 | Young et al. | 73/61 R |
| 3,497,728 | 2/1970 | Ostrofsky et al. | 73/644 X |
| 4,261,197 | 4/1981 | Mansfield | 73/61 R |
| 4,287,755 | 9/1981 | Mansfield | 73/61 R |
| 4,509,360 | 4/1985 | Erwin et al. | 73/61 R |

Primary Examiner—Stewart J. Levy
Assistant Examiner—Joseph W. Roskos
Attorney, Agent, or Firm—Glenn E. Klepac

[57] ABSTRACT

An apparatus and method for ultrasonically detecting inclusions in molten metals. The apparatus includes a probe comprising an inert refractory shell, a window supported by the shell for carrying ultrasonic waves between a coupling medium and a body of molten metal, and a coupling medium contained within the shell for carrying ultrasonic waves between a transducer and the window. A preferred apparatus utilizes a coupling medium comprising liquid gallium and is suitable for detecting inclusions in molten aluminum and aluminum alloys.

20 Claims, 2 Drawing Figures

APPARATUS AND METHOD FOR ULTRASONIC DETECTION OF INCLUSIONS IN MOLTEN METALS

BACKGROUND OF THE INVENTION

The present invention relates to apparatus and methods for ultrasonic detection of inclusions in molten metals.

Because particulate inclusions in molten metals often have a detrimental effect on metal quality, considerable effort has been devoted in recent years to developing apparatus and methods for detecting such inclusions. Some prior art devices for detecting particulate inclusions in molten metal are described in Young et al U.S. Pat. No. 3,444,726 and Mansfield U.S. Pat. Nos. 4,261,197 and 4,287,755. However, each of these prior art devices suffers from one or more serious limitations making it less than entirely suitable for its intended purpose.

For example, the devices relying upon a probe of titanium metal have a short operating life when used to detect inclusions in molten aluminum because titanium is soluble in aluminum. In addition, solid titanium and other solid metal probes usually contain grain boundaries, gas voids, inclusions and other impurities which may attenuate ultrasonic waves.

Another disadvantage of prior art devices is the need to provide a surface coating on the probe that is wettable by molten metal. Such surface coating causes an attenuation of the ultrasonic signals, thereby interfering with particle analysis.

A further limitation of prior art devices is the need to focus on a reflecting surface. Under production conditions, it is difficult to focus an ultrasonic beam and to maintain a reflective surface at a constant distance from the beam.

It is a principal objective of the present invention to obviate each of the above-mentioned disadvantages in the prior art.

One advantage of the probe described herein is that it is suitable for detecting particles in molten aluminum having a smaller effective particle size than with prior art devices.

Another advantage is that the apparatus and method described herein are suitable for use either with or without focusing a beam of ultrasonic waves. In addition, it is not necessary to have a reflecting surface.

A further advantage of a preferred probe of the invention is that it includes an amorphous silica window that is wetted by molten aluminum.

Additional advantages of the present invention will become apparent to persons skilled in the art from the following specification and drawings.

SUMMARY OF THE INVENTION

In accordance with the present invention, there is provided an apparatus for carrying ultrasonic waves between a transducer and a body comprising a molten metal or alloy. The apparatus includes a probe comprising an inert refractory shell, a window supported by the shell for carrying ultrasonic waves between a coupling medium and the body and a coupling medium contained within the shell for carrying ultrasonic waves between a transducer and the window.

The window comprises an interior surface portion contacting the coupling medium and an exterior surface portion that is wettable by the molten body. The acoustic attenuation factors for ultrasonic waves between the transducer and coupling medium, between the coupling medium and interior surface portion, between the interior and exterior surface portions, and between the exterior surface portion and the body are each less than about 3 dB. These attenuation factors are each preferably less than about 2 dB, more preferably less than about 1 dB and optimally as small as possible. The window preferably comprises amorphous silica.

In a preferred probe used for analysis of aluminum or aluminum alloys, the coupling medium comprises liquid gallium. The coupling medium preferably comprises a minor proportion of a metal solute dissolved in the gallium that reduces differences in acoustic impedance between the coupling medium, transducer and interior surface portion of the window. In a particularly preferred probe wherein the coupling medium comprises about 4.8 wt % silver dissolved in liquid gallium and the window is amorphous silica, the acoustic impedance of the coupling medium is approximately equal to the acoustic impedance of the interior surface portion and approximately equal to the acoustic impedance of the transducer.

The liquid gallium is preferably treated to remove oxides, solid inclusions and dissolved gases. Such treatment is desirable in order to minimize reflection of acoustic waves within the coupling medium. A probe containing liquid gallium has the advantage of lacking grain boundaries, gas voids, inclusions and other impurities found in solid metal probes.

A preferred apparatus includes a piezoelectric transducer capable of generating ultrasonic waves having a frequency of about 8-25 MHz. In order to maintain effective operation of the transducer it is spaced from the window, preferably by a distance of at least 10 cm. In addition, the preferred apparatus further comprises a cooling means for maintaining the transducer and liquid gallium adjacent thereto at a temperature below about 149° C. A probe having an inert refractory shell is capable of withstanding the caustic effects of molten aluminum and is sufficiently resistant to thermal stress for use with molten aluminum.

DETAILED DESCRIPTION OF A PREFERRED EMBODIMENT

Figure 1:
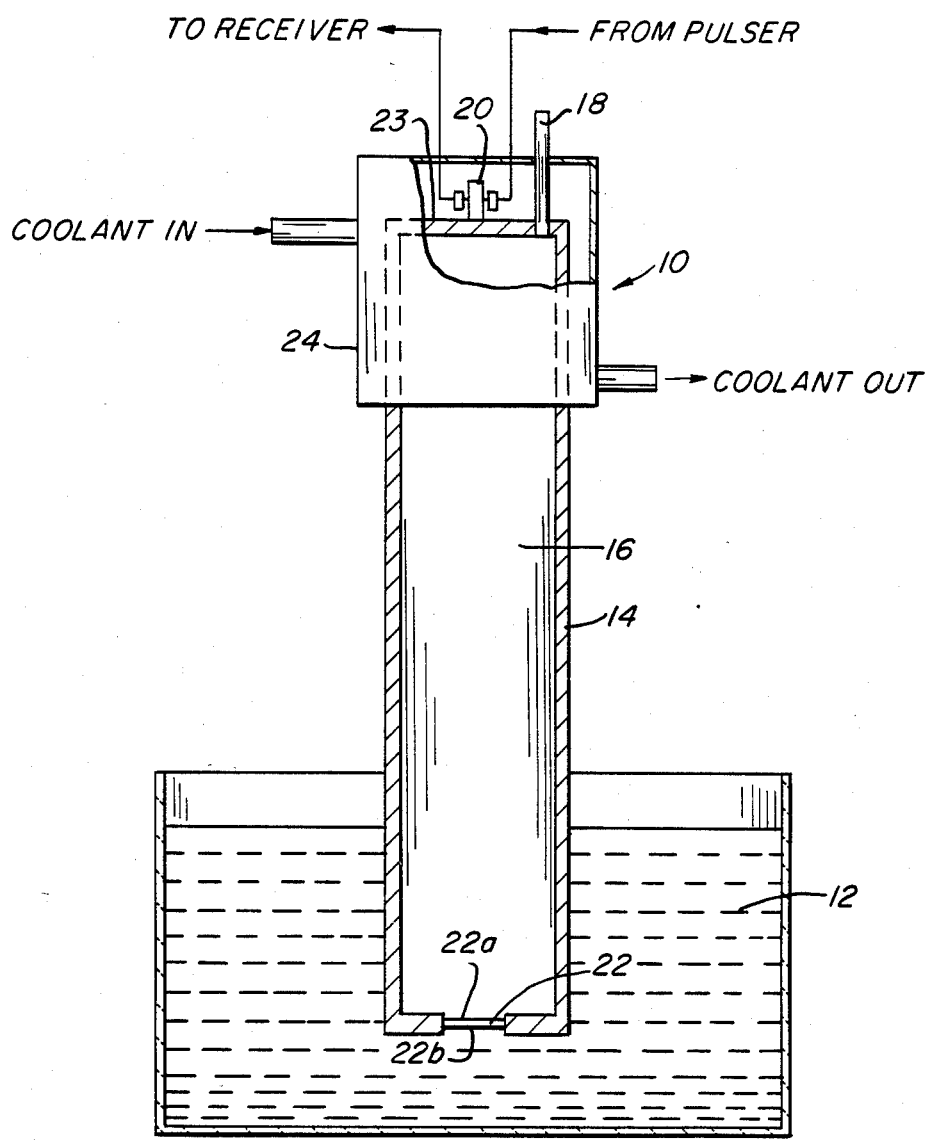
FIG. 1 is a schematic view of an apparatus for ultrasonic inspection of molten aluminum, including the probe of the present invention.

The probe 10 shown in FIG. 1 is used for detecting particulate inclusions in a body 12 comprising a molten metal or alloy. While the particular apparatus and method described herein are intended for detection of particulate inclusions in molten aluminum and aluminum alloys, the invention is not limited to use solely with aluminum or for detection of only particulate inclusions. The present apparatus and method are also probably suitable for ultrasonic testing of other metals and alloys having melting points below about 1,000° C., including but not limited to bismuth, gallium, indium, lead, lithium, magnesium, mercury, potassium, sodium, tin, zinc and their alloys. With appropriate modifications, the invention may also be applicable to ultrasonic testing of higher melting metals such as cobalt, copper, gold, iron, manganese, nickel, silver and their alloys.

Figure 2:
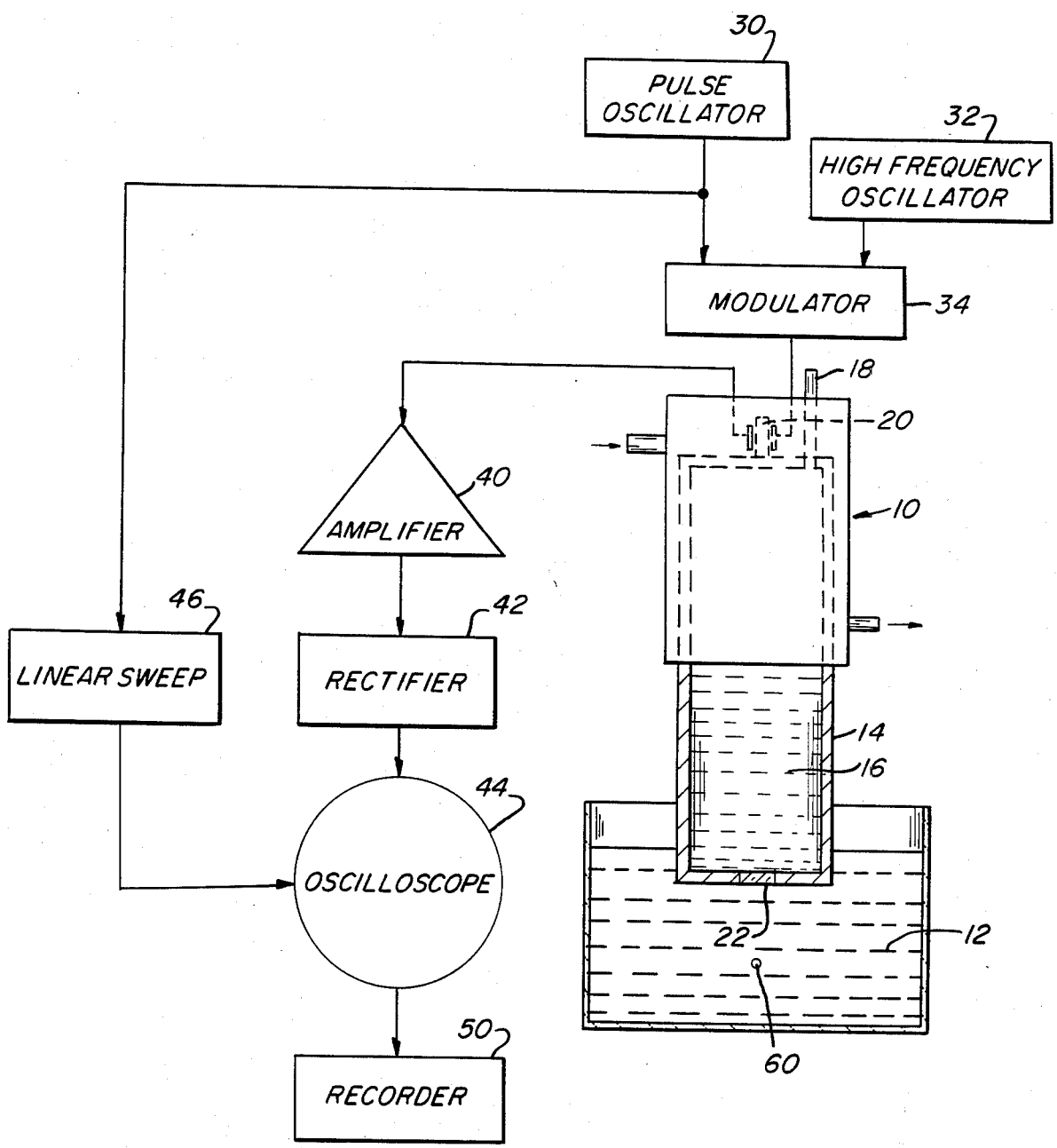
FIG. 2 is a schematic diagram of the apparatus and method of the invention.

Referring now to FIG. 2, the probe 10 comprises a hollow tubular refractory shell or envelope 14 containing a liquid metal coupling medium 16. The shell 14 is provided with an upwardly extending riser tube 18 in order to allow for expansion and contraction of the coupling medium 16 at different temperatures.

The shell 14 must be chemically inert both to the body 12 and coupling medium 16 at elevated temperatures. A preferred shell 14 is made from a predominantly alumina refractory material. This material is inert to aluminum alloys in the body 12 and to liquid gallium in the coupling medium 16 at elevated temperatures up to at least 800° C. The shell 14 may also be made from other inert refractories such as silica, silicon carbide and mullite.

A piezoelectric transducer 20 adjacent an upper end of the probe 10 sends ultrasonic waves through the coupling medium 16 to a window 22 spaced downwardly of the transducer 20. The preferred transducer 20 shown is a piezoelectric transducer. This transducer generates ultrasonic waves having a frequency of about 8-25 MHz in response to electrical stimuli. A particularly preferred operating frequency is about 15 MHz.

The transducer 20 is situated adjacent an amorphous silica upper wall or upper window 23 of the shell 14. The transducer 20 is fastened to the upper wall 23 by means of a high temperature adhesive.

Because the transducer 20 is sensitive to high temperatures, the probe 10 is provided with a cooling means or cooling jacket 24 for maintaining the transducer 20 and adjacent coupling medium 16 at a temperature at below about 149° C. The preferred probe 10 utilizes water as a coolant in the cooling means 24. The cooling means may be omitted entirely from the probe 10 if the apparatus is used for detection of inclusions in metals having low melting points such as bismuth, lithium or their alloys, or if a sufficiently large distance is maintained between the window and transducer 20 to insulate the transducer 20 from the generally hotter body 12. In a preferred probe 10 used for detecting inclusions in a molten aluminum alloy body 12 and having a liquid gallium coupling medium 16, the transducer 20 and window 24 should be separated by a distance of at least 10 cm. While it is desirable to maintain this distance as small as possible consistent with an acceptable thermal gradient, the distance must be increased in certain cases to avoid damaging the transducer 20. In the particularly preferred probe 10 described herein, the transducer 20 and window 22 are separated by a distance of about 15 cm.

The window 22 includes an interior surface portion 22a contacting the coupling medium 16 and an exterior surface portion 22b that is wettable by the body 12. It is contemplated that the interior surface portion 22a and exterior surface portion 22b will generally comprise a unitary structure, although composite structures are also within the scope of the invention. A unitary structure is preferred in order to minimize acoustic attenuation between the interior surface portion 22a and exterior surface portion 22b.

A particularly preferred window 22 is made from amorphous silica and has a cylindrical or disc shape. Silica has the advantage of being readily wetted by molten aluminum and its alloys.

The coupling medium 16 and window 22 are each made from materials which are selected to reduce acoustic attenuation between the transducer 20 and coupling medium 16, between the coupling medium 16 and window 22, and between the window 22 and body 12. As used herein, the term "acoustic attenuation factor" is defined by the following expression:

$$\Delta B = B_2 - B_1 = 10 \log \frac{I_2}{I_1}$$

wherein B is the acoustic intensity level in decibels and I is acoustic intensity of the sound waves, expressed in $W/m^2$.

The acoustic attenuation factors for ultrasonic waves between the transducer 20 and coupling medium 16, between the coupling medium 16 and window 22, and between the window 22 and body 12 should each be less than about 1 dB. In order to minimize acoustic attenuation between the transducer 20 and coupling medium 16 and between the coupling medium 16 and window 22, a minor proportion of a metal solute is dissolved in liquid gallium. The coupling medium 16 preferably comprises about 2.5-5 wt % silver dissolved in liquid gallium. The concentration of dissolved silver in the coupling medium 16 should generally be maintained below about 5 wt % in order to avoid precipitation of phases that might interfere with transmission of sound waves.

The gallium should be treated to remove oxides, solid inclusions and dissolved gases so that sound waves will be transmitted efficiently between transducer 20 and window 22.

The preferred coupling medium containing about 4.8 wt % silver dissolved in gallium has an acoustic impedance that is approximately equal to the acoustic impedance of the window and approximately equal to the acoustic impedance of the transducer 20. Accordingly, acoustic attenuation at interfaces between the transducer 20 and coupling medium 16 and between the coupling medium 16 and interior surface portion 22a is essentially zero. In addition, when the window 22 is made from amorphous silica, acoustic attenuation between the outer surface portion 22b and a body 12 of molten aluminum is calculated to be less than 1 dB. Accordingly, the probe of the invention is highly efficient for carrying ultrasonic waves between the transducer 20 and body 12 without thermal damage to the transducer 20.

The coupling medium 16 preferably has a low vapor pressure at the temperature of the body 12. Liquids having significant vapor pressure at elevated temperatures may form bubbles that would interfere with transmission of ultrasonic wave trains through the coupling medium. An advantage of liquid gallium is that its boiling point is 2403° C. Accordingly, a coupling medium comprising a principal proportion of liquid gallium has low vapor pressure even at temperatures up to about 732° C. (1350° F.), the highest temperature at which aluminum alloys are usually maintained.

Referring now to FIG. 2, the apparatus further comprises a voltage pulse oscillator 30, a high frequency oscillator 32 generating alternating voltage of ultrasonic frequency, and a modulator 34 receiving electrical pulses from the voltage pulse oscillator 30 and a high frequency oscillator 32. The modulator 34 generates a direct current voltage train having a voltage of about 300 volts by passing voltage of ultrasonic frequency only during the period that the modulator 34 is receiving a pulse from the voltage pulse oscillator 30. This direct current voltage train energizes the transducer 20.

In the preferred apparatus shown, the transducer 20 also acts as a receiving transducer for receiving wave trains from the body 12 through the window 22 and coupling medium 16. The receiving transducer 20 then generates voltage trains in response to wave trains received from the body 12. The voltage trains so generated are sent to an amplifier 40, rectifier 42 and oscilloscope 44. A linear sweep circuit 46 synchronized with the voltage pulse oscillator 30 is connected to the oscilloscope 44. The oscilloscope 44 has a spot that is deflected in one direction by the sweep circuit 46 and deflected in a different direction by the voltage output from the receiving transducer 20. A permanent record of the oscilloscope display is maintained in a recorder 50. In FIG. 1, the voltage pulse oscillator 30, high frequency oscillator 32 and modulator 34 are referred to collectively as a "pulser". The amplifier 40, rectifier 42, oscilloscope 44 and sweep circuit 46 are similarly called "receiver".

A description of the operation of a similar system for sending and receiving pulses to and from the transducer 20 is described in Firestone U.S. Pat. No. 2,280,226, which patent is incorporated by reference to the extent not inconsistent with the present invention.

As shown in FIG. 2, ultrasonic waves generated by the transducer 20 are transmitted through the coupling medium 16 and window 22 into a body 12 of molten aluminum. When these ultrasonic waves strike a suspended particle or particulate inclusion 60, extra vibration wave trains are sent back to the transducer 20 and voltage trains are generated in response to such ultrasonic wave trains. The voltage trains are then displayed on the oscilloscope 44.

An advantage of the probe 10 described herein is that it is so efficient at transmitting ultrasonic wave trains that the claimed apparatus detects smaller particles 60 than prior art apparatus. The probe 10 consistently detects solid particulate inclusions having an effective diameter of less than about 400 microns, and particles as small as about 50 microns have been detected in molten aluminum. The probe 10 is theoretically capable of detecting particles in about the 1–10 micron diameter range.

While the present invention has been described in terms of preferred embodiments, it will be apparent to persons skilled in the art that modifications and adaptations can be made within the scope of the present invention without departing from the spirit of the following claims.

What is claimed is:

1. A probe for carrying ultrasonic waves between a transducer and a body comprising a molten metal or alloy, said probe comprising
   (a) a refractory shell, said shell being inert to molten metals,
   (b) a coupling medium for carrying ultrasonic waves between a transducer and a window spaced from said transducer, said coupling medium comprising a liquid metal contained within said shell, the acoustic attenuation factor for ultrasonic waves between the transducer and coupling medium being less than about 3 dB,
   (c) a window for carrying ultrasonic waves between said coupling medium and said body, said window being supported by said shell and comprising
      (1) an interior surface portion contacting said coupling medium, the acoustic attenuation factor for ultrasonic waves between said coupling medium and said interior surface portion being less than about 3 dB, and
      (2) an exterior surface portion wettable by said body, the acoustic attenuation factors for ultrasonic waves between said interior and exterior surface portions and between said exterior surface portion and said body each being less than about 3 dB.

2. The probe of claim 1 wherein said body comprises aluminum or an aluminum alloy and said coupling medium comprises liquid gallium.

3. The probe of claim 2 wherein said coupling medium further comprises a minor proportion of a metal solute dissolved in said liquid gallium.

4. The probe of claim 3 wherein the acoustic impedance of the coupling medium is approximately equal to the acoustic impedance of the interior and exterior surface portions and approximately equal to the acoustic impedance of the transducer.

5. The probe of claim 3 wherein the metal solute dissolved in liquid gallium comprises silver.

6. The probe of claim 5 comprising about 2.5–5 wt % silver dissolved in the liquid gallium.

7. The probe of claim 2 wherein the acoustic attenuation factors for ultrasonic waves between the transducer and coupling medium, between said coupling medium and said interior surface portion, between said interior and exterior surface portions and between said exterior surface portion and said body are each less than about 2 dB.

8. The probe of claim 2 wherein the acoustic attenuation factors for ultrasonic waves between the transducer and coupling medium, between said coupling medium and said interior surface portion, between said interior and exterior surface portions and between said exterior surface portion and said body are each less than about 1 dB.

9. The probe of claim 2 wherein said window comprises amorphous silica.

10. An apparatus for transmitting ultrasonic waves into a molten body comprising molten aluminum or an aluminum alloy and for receiving waves reflected within said body in order to determine the presence or absence of solid inclusions in said body, said apparatus comprising the probe of claim 2 and
    (d) a piezoelectric transducer adjacent said liquid gallium, said transducer being spaced from said window.

11. The apparatus of claim 10 wherein said transducer is spaced from said window by a distance of at least 10 cm.

12. The apparatus of claim 10 further comprising
    (e) cooling means for maintaining the transducer and the liquid gallium adjacent thereto at a temperature below about 149° C.

13. The apparatus of claim 12 further comprising
    (f) a voltage pulse oscillator,
    (g) a high frequency oscillator generating alternating voltage of ultrasonic frequency,
    (h) a modulator receiving electrical impulses from said voltage pulse oscillator and said high frequency oscillator, said modulator generating a voltage train by passing said voltage of ultrasonic frequency only during the period that the modulator is receiving a pulse from said voltage pulse oscillator, said voltage train energizing said transducer, (i) a receiving transducer actuated by vibration wave trains received from said body and generating voltage trains in response to said wave trains, (j) a sweep circuit synchronized with said voltage pulse oscillator, and (k) an oscilloscope whose spot is deflected in one direction by said sweep circuit and is deflected in a different direction by the voltage output from said receiving transducer.

14. A process for ultrasonically inspecting a body comprising a molten metal or alloy, said process comprising (a) generating ultrasonic waves with a piezoelectric transducer, (b) transmitting said waves from said transducer to a window spaced therefrom through a coupling medium comprising a liquid metal, the acoustic attenuation factor for ultrasonic waves between the transducer and coupling medium being less than about 3 dB, (c) transmitting said waves through a window into a body comprising a molten metal or alloy, said window comprising (1) an interior surface portion contacting said coupling medium, the acoustic attenuation factor for ultrasonic waves between said coupling medium and said interior surface portion being less than about 3 dB, and (2) an exterior surface portion wetted by said body, the acoustic attenuation factors for ultrasonic waves between said interior surface portion and said exterior surface portion and between said exterior surface portion and said body each being less than about 3 dB, and (d) receiving and interpreting reflections of said waves after their emergence from said body.

15. The process of claim 14 wherein said body comprises molten aluminum or an aluminum alloy and said coupling medium comprises liquid gallium.

16. The process of claim 15 wherein said coupling medium further comprises about 2.5–5 wt % of silver dissolved in said gallium.

17. The process of claim 15 wherein the frequency of said ultrasonic waves is about 8–25 MHz.

18. The process of claim 15 wherein step (d) includes reflecting said ultrasonic waves from a particulate inclusion suspended in said body, said inclusion having an effective diameter of less than about 400 microns.

19. The process of claim 15 wherein said window comprises amorphous silica and wherein the acoustic impedances of said transducer, said coupling medium, and said window are approximately equal to one another.

20. The process of claim 15 wherein the acoustic attenuation factors for ultrasonic waves between the transducer and coupling medium, between said coupling medium and said interior surface portion and between said interior and exterior surface portions are each less than about 2 dB.

* * * * *